United States Patent [19]

West et al.

[11] Patent Number: 5,023,387

[45] Date of Patent: Jun. 11, 1991

[54] LIQUID FEED INJECTION IN A CHLOROMETHANES PROCESS

[75] Inventors: David H. West; Lawrence A. Hebert, both of Baton Rouge; Roger L. Bowlin, Denham Springs; Michael T. Holbrook, Baton Rouge, all of La.

[73] Assignee: The Dow Chemical Company, Midland, Mich.

[21] Appl. No.: 517,000

[22] Filed: Apr. 30, 1990

Related U.S. Application Data

[63] Continuation-in-part of Ser. No. 342,252, Apr. 24, 1989, abandoned.

[51] Int. Cl.$^5$ .............................................. C07C 17/10
[52] U.S. Cl. ................................................... 570/252
[58] Field of Search ............................... 570/252, 255

[56] References Cited

U.S. PATENT DOCUMENTS 2,829,180  4/1958  Montgomery et al. ............. 260/662
2,857,438  10/1958  Obrecht et al. ..................... 260/654

FOREIGN PATENT DOCUMENTS 57-142927  9/1982  Japan .

OTHER PUBLICATIONS

*Kirk–Othmer Encyclopedia of Chemical Technology,* 3rd Edition, vol. 5, John Wiley and Sons (1979), pp. 680–681, 688–689, 697–698.

*Primary Examiner*—Howard T. Mars

[57] ABSTRACT

An adiabatic vapor phase chlorination of methylene chloride, methyl chloride or a mixture thereof is improved by the injection of a portion of the methylene chloride, methyl chloride or mixture thereof into the reactor in the liquid state under conditions such that the temperature throughout the reaction zone is maintained at less than about 500° C.

13 Claims, No Drawings

LIQUID FEED INJECTION IN A CHLOROMETHANES PROCESS

CROSS-REFERENCE TO RELATED APPLICATION

This application is a continuation-in-part of co-pending application, Ser. No. 342,252, filed Apr. 24, 1989 now abandoned.

BACKGROUND OF THE INVENTION

This invention is related to processes for the preparation of chloromethanes such as methylene chloride and chloroform by the thermally initiated vapor phase chlorination of methyl chloride and methylene chloride.

Vapor phase chlorination of methyl chloride and methylene chloride in an adiabatic reactor is generally known. The exothermicity of such reactions is well known and can result in serious problems including carbonization of the products and by-product formation as well as explosive hazards. One method of controlling the exothermic nature of the reaction is to limit the chlorine concentration which in turn limits the extent of the reaction. Such a limitation placed on chlorine concentration also limits other reaction parameters such as product mix and the amount of methyl chloride and methylene chloride which may be converted per pass through the reactor. An additional problem associated with vapor phase chlorination is incomplete conversion of the chlorine. The presence of even very small amounts of chlorine in the process downstream of the chlorination reactor can be extremely detrimental to equipment and can produce undesirable impurities in the products.

Various approaches to improving chlorination processes have been proposed. U.S. Pat. No. 2,829,180 teaches the use of a fluidized bed along with an inert diluent, in liquid or vapor form, to control the explosive tendencies of the reaction of chlorine and methane. The primary focus of this process is to produce a product containing a predominating proportion of chloroform. U.S. Pat. No. 2,857,438 teaches the use of liquid coolant in a process for the preparation of perchlorinated products such as carbon tetrachloride and tetrachloroethylene. The primary goal of this process is to produce a product containing high yields of carbon tetrachloride and tetrachloroethylene while minimizing yields of various by-products such as chloroform.

As is clear from a review of these references, the results desired and the process steps capable of obtaining desired results vary from process to process. Thus, what is needed is an improved method for the adiabatic vapor phase chlorination of methyl chloride and methylene chloride that eases the limits placed on chlorine concentration; gives flexibility in product mix; and improves reactor volumetric efficiency.

SUMMARY OF THE INVENTION

The present invention is such an improved process for the thermally initiated adiabatic vapor phase chlorination of methyl chloride, methylene chloride and mixtures thereof wherein the improvement comprises injecting a portion of the methyl chloride, methylene chloride or mixtures thereof into a chlorination reactor in the liquid phase under reaction conditions such that the temperature throughout the reaction zone of the reactor is maintained at equal to or less than about 500° C. without the presence of hot spots. The reaction zone temperature is preferably greater than about 200° C.

An advantage of the present invention is the ability to affect product distribution and yield in existing processes without the need for expensive modifications to existing plants and equipment.

DETAILED DESCRIPTION OF ILLUSTRATIVE EMBODIMENTS

In commercial processes for the adiabatic chlorination of organic reactants, the product distribution and yield are primarily controlled by the chlorine concentration, the concentration of the organic reactants and the particular configuration of the plant being used. The practice of the improved process of the present invention, i.e., introducing a portion of the organic reactants in the liquid phase, adds an additional factor which can be used to affect the product yield and distribution. The amount and identity of the organic feed injected as a liquid affects product yield and distribution.

The process of the present invention is an improved vapor-phase, thermally initiated chlorination of an organic feed, which is methyl chloride, methylene chloride or a mixture thereof, in an adiabatic reactor to produce chloroform and methylene chloride. With the exception of the improvement comprising the injection of a portion of the organic feed in liquid form, the particular process followed is not critical to the invention and is generally any thermally initiated chlorination process known to those skilled in the art. Such processes are discussed, for example, in *Kirk-Othmer Encyclopedia of Chemical Technology*, 3rd Edition, Volume 5, John Wiley and Sons (1979) on pages 680–681, 688–689 and 697–698. Typically, in such processes, chlorine and an excess of the organic feed are fed into a reactor, preferably a cylindrical reactor constructed of a high nickel alloy or refractory lined steel, and react to form hydrogen chloride, methylene chloride, chloroform, carbon tetrachloride and various byproducts. The reactor is preheated to a temperature sufficient for initiating the reaction which is preferably about 300° C. to 400° C. prior to the introduction of the reactants. Once started, no additional heating is necessary.

The feed temperature is advantageously controlled so as to just exceed the dew point of the feed mixture which is evaluated at the pressure just upstream of the reactor. Reactor outlet temperature is controlled in the range 400° C.–500° C. This is typically done by adjusting the flow of chlorine which controls the extent of reaction and thus the temperature obtained in the reactor. Outlet temperatures above about 500° C. significantly increase the rate of formation of carbonaceous material and other undesirable products. Further, since the reaction is highly exothermic, it is desirable to control the temperature of the reaction zone to prevent explosive hazards. Thus, the reactor outlet temperature is maintained at less than about 500° C., more preferably less than about 490° C. By the practice of this invention, the temperature throughout the reactor is maintained at less than about 500° C., preferably less than about 490° C.

Any ratio of methyl chloride to methylene chloride is useful as the organic feed in the practice of this invention. This would include using either methylene chloride or methyl chloride exclusively as well as using mixtures of the two. It is preferred that the mole ratio of methyl chloride to methylene chloride range from about 1.5 to about 5.0. The methylene chloride and/or methyl chloride may be supplied in relatively pure form or may be supplied as recycled materials from the reaction itself. In the case wherein the reactants are recycled, they may contain various contaminants in small amounts without significantly detrimentally impacting the process. Examples of these include chloroform, carbon tetrachloride and other products or by-products of the chlorination reaction.

In adiabatic reactions of this type, the ratio of methyl chloride to methylene chloride as well as the chlorine concentration present affects the product distribution and yield. In commercial operations, various factors constrain the ratio of methyl chloride to methylene chloride that is practical to use including the source of each. In particular, when a portion of one or both are supplied as recycle feeds, the capability of the plant to recycle the material limits the feed composition and thus limits the product yield and distribution available without modification of the physical plant.

In addition to the ratio of methylene chloride to methyl chloride in the organic feed and the physical plant configuration, a significant variable affecting the relative yields of the products is chlorine concentration. A major limitation on chlorine concentration is due to the temperature restrictions discussed above. These result from the exothermic nature of the reaction between chlorine and methylene chloride and methyl chloride. Since the organic feed is used in a stoichiometric excess, the concentration of chlorine controls the extent of the reaction in the present process and thus controls the temperature reached in the reactor which is preferably limited to 500° C. or less.

The improved process of this invention increases the chlorine concentration that may be used by injecting a portion of the organic feed in the liquid phase. The portion of the organic feed injected in the liquid phase vaporizes under reaction conditions. Part of the heat of reaction is thus taken up by the sensible heat of the liquid, the heat of vaporization of the liquid, and the sensible heat of the vapor resulting from the evaporation of the liquid organic feed. The chlorine concentration can thus be increased thus increasing the extent of the reaction while the outlet reactor temperature and the temperature throughout the reactor is maintained at temperatures below about 500° C.

The amount by which the chlorine concentration may be increased by the process of this invention varies depending on process parameters. Any increase in chlorine concentration and thus the extent of reaction or amount of organic feed converted to product is desirable. It is preferred that the chlorine concentration is increased by at least about 3 percent by the practice of this invention and more preferred that it is increased by at least about 10 percent. In a typical commercial process for the chlorination of a mixture of methyl chloride and methylene chloride without liquid injection where the chlorine concentration is limited to a mole fraction of about 0.24, the mole fraction can be increased by at least about 12 percent to 0.27 or more by injecting a portion of the organic feed as a liquid spray. While the exact increases that may be obtained depend on the particular process constraints, other processes using other conditions would result in comparable percentage increases.

The chlorine concentration in the feed stream cannot be increased without limit by the practice of this invention. This is due, at least in part, to the fact that when the chlorine concentration in the feed stream exceeds a particular amount, there is a danger of combustion or detonation. The chlorine concentration in the feed stream that is feasible without exceeding its flammability limit is a function of various factors including the mole fraction of methylene chloride present in the organic feed in the gas phase. Other factors affecting the flammability limit include reactor configuration, design, temperature and pressure.

Empirically it has been found that a safe concentration of chlorine in the feed stream increases with increases in the concentration of methylene chloride in the gas feed. For a given overall methyl chloride to methylene chloride feed ratio, the injection of a portion of the methyl chloride in the liquid phase increases the concentration of methylene chloride in the gas phase. This, in turn, permits a higher concentration of chlorine in the feed stream to be used safely. Conversely, when a portion of the methylene chloride is injected as a liquid, the concentration of methylene chloride in the vapor phase decreases, thus resulting in a lower safe chlorine concentration in the feed stream. For this reason, the injection of liquid methyl chloride enables a somewhat broader range of operating conditions than is safely obtainable when methylene chloride is used as the injected liquid feed. However, the injection of either methyl chloride, methylene chloride or their mixture as a liquid results in higher chlorine concentrations being operable while the temperature throughout the reactor is maintained at less than about 500° C.

Since the heat of evaporation of a liquid is a function of the identity of the liquid, the mole fraction of the organic feed that is injected as liquid to permit a particular chlorine concentration to be used will vary depending on the liquid injected. Other factors that are important include the reactor conditions such as temperature and pressure. Generally, the injection of any percentage of the organic feed as a liquid will result in cooling which will enable the use of higher chlorine concentrations while maintaining desired temperatures within the reactor. Preferably, the amount of the organic feed injected as a liquid is at least about 5 mole percent of the total organic feed and preferably no more than about 60 mole percent.

In addition to permitting the use of higher chlorine concentrations, the injection of a portion of the organic feed in liquid form preferably results in improved chlorine conversion and thus improved volumetric efficiency of the reactor.

The portion of the organic feed injected as a liquid is not available for reaction until it has vaporized. This is due, at least in part, to the temperatures required for thermally initiated chlorination used in this process. Thermally initiated chlorination of methylene chloride and methyl chloride such as that practiced in this invention requires temperatures of at least about 200° C. to proceed at a reasonable rate. The liquid feed of this invention, even if superheated, exists only at temperatures significantly below this. Therefore, it is necessary that the liquid portion of the organic feed evaporates in a time period which is short compared to the reaction time if it is to be available as a reactant. Additionally, the organic vapor produced from the evaporating liquid must become mixed with the other reactants in a time that is short compared to the reaction time.

Thus, the manner in which the liquid organic feed is injected affects its availability as a reactant. This in turn affects product distribution and yields. The rate of evaporation of the organic feed injected as a liquid also influences its effectiveness in cooling the reactor so that the temperature throughout the reactor is maintained at less than about 500° C. while maintaining a higher chlorine concentration than would be feasible without the cooling so provided.

Various factors are important in controlling the rate at which the liquid feed vaporizes and mixes with the other reactants. These include the manner in which the liquid is introduced into the reactor, the temperature and pressure of the liquid as it is injected, the conditions inside the reactor and the identity of the liquid feed.

Proper atomization plays a key role in controlling the time required for evaporation. An important factor in obtaining proper atomization is the means by which the liquid portion of the organic feed is introduced into the reactor. While other means may be useful, it is preferred to inject the liquid into the reactor using a nozzle. In a preferred embodiment, atomizing nozzles are selected to be capable of producing droplets with a Sauter mean diameter of at least about 30 microns and no more than about 200 microns under operating conditions. It is more preferred that droplets having a Sauter mean diameter of less than about 100 microns are produced. Examples of nozzles useful in the practice of this invention include pressure swirl type hydraulic nozzles such as those manufactured by the Delavan Corporation and simple orifice type nozzles which may be obtained by machining from bar metal. Other examples include hydraulic nozzles such as those manufactured by Bete Fog Nozzle Incorporated and more elaborate two-fluid atomizing nozzles such as those in which the liquid is introduced into the throat of a venturi tube. The actual design of the atomizing nozzle is less important than its ability to produce the desired drop size at the relevant operating conditions. Thus, no advantage is gained by using any more elaborate device than is necessary. The liquid feed line and attached atomizing nozzle are preferably placed inside the normal vapor feed line in a coaxial arrangement.

The preferred atomizing nozzle is dependent upon the identity of the liquid organic feed being injected. For example, liquid methylene chloride is preferably injected through a pressure swirl or other efficient type of atomizing nozzle. Liquid methyl chloride may preferably be injected using a simple orifice of sufficiently small diameter so that the operating pressure on the upstream side of the nozzle is at least about 20 psi (0.14 kg/cm$^2$) and more preferably at least about 60 psi (0.42 kg/cm$^2$) above the reactor operating pressure immediately downstream from the nozzle.

In some embodiments, it may be desirable to heat the liquid organic feed prior to injecting it into the reactor. In these embodiments, it is preferred that the pressure on the upstream side of the nozzle is greater than the saturation pressure of the liquid organic feed evaluated at the temperature of the reactor immediately downstream from the nozzle.

Additional factors influencing the evaporation rate of the injected liquid organic feed include the velocity of the injected liquid relative to the velocity of the vapor and the initial trajectory of the liquid feed being injected. In a preferred embodiment, the vapor feed is introduced into the reactor at a velocity of at least about 30 feet per second (9.1 meters per second). The upper limit on vapor velocity is sonic velocity. It is preferred that the vapor velocity is at least about 75 feet per second (22.9 meters per second) and more preferred that it is at least about 200 feet per second (61.1 meters per second).

The velocity of the vapor feed is related to the level of turbulence present in the reactor. This turbulence is also important in promoting efficient evaporation and mixing. A vapor flow having a preferred velocity and sufficient turbulence can be obtained by proper selection of the vapor feed nozzle. Generally the vapor feed nozzle should have a diameter which is relatively small in comparison to the reactor diameter. It is preferred that the vapor feed nozzle has a diameter less than about one-fifth that of the reactor and more preferred that the vapor feed nozzle has a diameter less than about one-eighth that of the reactor. One skilled in the art will recognize that additional methods may be useful in obtaining a vapor flow with a high degree of turbulence. In plant scale reactors, a high degree of turbulence may be inherent in the plant design.

The initial trajectory of the liquid feed being injected into the reactor is also important in determining the rate of evaporation. In the practice of this invention, it has been found that spray angles of about 60 degrees or more result in maximum cooling within and surrounding the reaction zone. Spray angles of less than about 30 degrees concentrate the spray along the center line of the reactor and result in higher temperatures within and around the reaction zone than the use of the wider angles of injection.

The rate of evaporation is, of course, related to the degree of cooling within the reaction zone with faster evaporation generally having a positive relationship with a greater degree of cooling. Further, the various factors affecting rate of evaporation are themselves related. Thus, the effects of spray angle, relative velocity of the liquid and vapor and the drop size distribution of the resulting liquid spray are not independent. Various combinations of these variables can be employed to produce the desired results in various circumstances as will be well recognized by one skilled in the art.

It is anticipated that, in some cases, it may be beneficial to utilize a narrow spray angle or high liquid velocity (relative to the vapor velocity) or some combination thereof in order to limit the degree of cooling within the reactor. For example, in some processes for the chlorination of methyl chloride and methylene chloride, it may be desirable to operate with the most vigorous reaction conditions possible in order to minimize the size of the reaction zone and thus the required reactor volume.

In a preferred embodiment of the present invention, methylene chloride and methyl chloride, supplied in the vapor state from suitable evaporators, are separately flow controlled and then mixed prior to entering a knockout drum. The methylene chloride and methyl chloride vapor mixture is then superheated using an appropriate heat exchanger and then fed through a vapor feed nozzle into a reactor constructed of a high nickel alloy or refractory lined steel. All transfer lines between the feed evaporators and the reactor are traced with steam.

Chlorine gas is supplied to the reactor in two separate lines. The primary chlorine feed is used to control the reactor outlet temperature. That is, the rate of the primary chlorine feed is increased or decreased as necessary to maintain the reactor outlet at the desired temperature. The secondary chlorine feed is controlled at a fixed ratio to the liquid organic feed. By this, it is meant that the secondary chlorine feed is automatically adjusted based on the amount of the organic feed that is injected, in the liquid state, directly into the reactor. As discussed above, the injection of a portion of the organic feed in the liquid state permits a higher concentration of chlorine to be used without the outlet reactor temperature exceeding a temperature which results in excessive carbon and byproduct formation. The two chlorine flows are recombined prior to mixing with the organic vapor feed. The chlorine feed is injected through a nozzle which tees into the organic feed line located upstream of the reactor inlet.

A centrifugal pump is used to supply the liquid organic feed which may be methyl chloride or methylene chloride at the appropriate pressure. The liquid is flow controlled at the desired rate and fed into the reactor through an atomizing nozzle positioned inside, and parallel to, the vapor feed nozzle.

The reactor effluent is quenched using an air cooled heat exchanger. The reactor pressure is controlled using a pressure control valve mounted on the outlet of the air cooler. The reactor itself is typically constructed of a nickel chromium alloy.

One particular embodiment comprises the reaction of a mole fraction of chlorine in the feed ranging from about 0.24 to about 0.28 with an organic feed comprising methyl chloride and methylene chloride in a mole ratio ranging from about 1.5 to about 2.0 wherein from about 0.08 to about 0.16 mole fraction of the total organic feed is injected as a liquid and in the absence of additional cooling.

Another particular embodiment comprises the reaction of a mole fraction of chloride in the feed ranging from about 0.24 to about 0.30 with an organic feed comprising methyl chloride and methylene chloride in a mole ratio ranging from about 4 to about 5 wherein from about 0.40 to about 0.60 mole fraction of the total organic feed is injected as a liquid and in the absence of additional cooling.

The following examples are provided to further illustrate the invention and should not be interpreted as limiting it in any way. Unless stated otherwise, all parts and percentages are by mole.

EXAMPLE 1

Liquid Injection of Methyl Chloride

Liquid methyl chloride and liquid methylene chloride are each individually evaporated and their vapors are mixed and then superheated to about 60° C. Chlorine gas is mixed with the organic vapor feed well upstream of the reactor. The chlorine gas is provided through two separate lines. The primary line is used to control the reactor outlet temperature and the make-up line is ratio controlled to the liquid injection feed. As the liquid injection of the organic feed is increased, the chlorine concentration in the make-up line is increased. The two chlorine lines are combined prior to mixing with the organic vapor feed. The liquid organic feed, methyl chloride, is supplied at 350 psig via a centrifugal pump. The liquid feed is supplied to the reactor via an atomizing nozzle having a 0.028 orifice. The ratio of methyl chloride to methylene chloride (including both liquid and vapor) is 1.5. The mole fraction of $Cl_2$ in the feed is varied from about 0.22 to about 0.28 in various runs as shown in Table I below. When the mole fraction of $Cl_2$ in the feed is less than about 0.24, none of the organic feed is being injected in the liquid state. When the mole fraction of $Cl_2$ is about 0.28, the liquid mole fraction in the total organic feed is about 0.20.

A nickel chromium reactor is used. The reactor is preheated to 400° C. under a nitrogen flow using electric tracing prior to start up. It is then purged with methyl chloride before introducing chlorine. The reaction starts with a minimum chlorine concentration of about 18 percent. The injection of the liquid methyl chloride is started at 10 lb/hr, the minimum controllable flow rate. The temperature inside the reactor drops about 10° C.-20° C. when the liquid flow is started. Chlorine concentration is increased to offset the temperature reduction due to the liquid flow.

Reactor residence time is about 5.5 seconds and the total reactant flow rate through the reactor is about 300 lb/hour. Pressure in the reactor is maintained at about 40 psig. Samples of the reactor effluent are examined by gas chromatography.

The product distribution obtained varies depending on the mole fraction of chlorine in the feed. At a mole fraction of chlorine feed of 0.23, of methyl chloride of 0.46 and of methylene chloride of 0.31, and wherein no methyl chloride is injected as a liquid, the product distribution is as follows:

| | |
|---|---|
| methyl chloride | 0.437 |
| methylene chloride | 0.453 |
| chloroform | 0.101 |
| carbon tetrachloride | 0.008 |

At a mole fraction of chlorine feed of 0.29, of methyl chloride of 0.43 and of methylene chloride of 0.28, and wherein a portion of the methyl chloride is injected as a liquid, the product distribution is as follows:

| | |
|---|---|
| methyl chloride | 0.390 |
| methylene chloride | 0.444 |
| chloroform | 0.148 |
| carbon tetrachloride | 0.018 |

EXAMPLE 2

Liquid Injection of Methyl Chloride

Example 1 is repeated with the exception that the ratio of methyl chloride to methylene chloride is 2.0 rather 1.5. In this example, the mole fraction of chloroform present in the product is found to be 0.085 at a chlorine concentration of 0.22 (no liquid injection): 0.133 at a chlorine concentration of 0.28 (liquid injection); and 0.142 at a chlorine concentration of 0.30 (liquid injection).

EXAMPLE 3

Liquid Injection of Methylene Chloride

The general procedure outlined in Example 1 is followed with the exception that a portion of the methylene chloride rather than methyl chloride is injected as a liquid. The results obtained are shown in Table I below

TABLE I

| Mole Fraction Cl$_2$ | M1/M2 Ratio[1] | n$_1$/n$_0$[2] | Product | Mole Fraction Product | Increase in Chloroform |
|---|---|---|---|---|---|
| 0.23 | 1.5 | — | Methyl chloride | 0.410 | — |
|  |  |  | Methylene chloride | 0.483 |  |
|  |  |  | Chloroform | 0.099 |  |
|  |  |  | Carbon tetrachloride | 0.008 |  |
| 0.25 | 1.5 | 0.08 | Methyl chloride | 0.398 | 14% |
|  |  |  | Methylene chloride | 0.478 |  |
|  |  |  | Chloroform | 0.113 |  |
|  |  |  | Carbon tetrachloride | 0.011 |  |
| 0.27 | 1.5 | 0.16 | Methyl chloride | 0.382 | 23% |
|  |  |  | Methylene chloride | 0.483 |  |
|  |  |  | Chloroform | 0.122 |  |
|  |  |  | Carbon tetrachloride | 0.014 |  |
| 0.25 | 2.0 | — | Methyl chloride | 0.447 | — |
|  |  |  | Methylene chloride | 0.454 |  |
|  |  |  | Chloroform | 0.092 |  |
|  |  |  | Carbon tetrachloride | 0.008 |  |
| 0.28 | 2.0 | — | Methyl chloride | 0.415 | 25% |
|  |  |  | Methylene chloride | 0.456 |  |
|  |  |  | Chloroform | 0.115 |  |
|  |  |  | Carbon tetrachloride | 0.014 |  |

[1]Ratio of methyl chloride to methylene chloride.
[2]Liquid mole fraction in total organic feed.

The information in Examples 1-3 demonstrates that the injection of a portion of the organic feed in the liquid state results in increased yields of chloroform. Increases in chloroform production range from 14 to 25 percent.

EXAMPLE 4

Reduction in Cl$_2$ Concentration in Effluent

The general procedure outlined in Example 1 is followed In different runs, portions of the methylene and methyl chloride respectively are injected as liquids. In other runs, none of the organic feed is injected in the liquid state. The reactor effluents are analyzed for the presence of chlorine measured as parts per million (ppm) by weight. The results obtained are shown in Table II below.

TABLE II

| Mole Fraction Cl$_2$ | M1/M2 Ratio[1] | Residence Time | n$_1$/n$_0$[2] | Cl$_2$ in Effluent (ppm) | % Decrease in Cl$_2$ in Effluent |
|---|---|---|---|---|---|
| 0.25 | 2.0 | 5.40 | — | 533 | — |
| 0.28 | 2.0 | 5.05 | 0.11[3] | 275 | 48 |
| 0.27 | 2.0 | 5.19 | 0.16[4] | 192 | 64 |

[1]Ratio of methyl chloride to methylene chloride.
[2]Liquid mole fraction in total organic feed.
[3]Liquid methylene chloride injected.
[4]Liquid methyl chloride injected.

The data in Table II above demonstrates that the injection of a portion of the organic feed as a liquid results in a significant decrease in the chlorine concentration of the reactor effluent.

EXAMPLE 5

Injection of a Mixture of Methyl Chloride and Methylene Chloride

The general procedure outlined in Example 1 is followed with the following exceptions: (1) the organic feed injected is a mixture of methyl chloride and methylene chloride: (2) the chlorine, vapor organic feeds and liquid organic feeds are mixed simultaneously within the throat of a venturi tube which is attached directly to the inlet of the reactor; and (3) the reactor pressure is controlled between 70 and 90 psig and the inlet temperature is maintained between 75° C. and 85° C. The results obtained are shown in Table 111 below.

TABLE III

| Mole Fraction Cl$_2$ | M1/M2 Ratio[1] | Residence Time (Second) | Mole Fraction M2 in Liquid | n$_1$/n$_0$[2] | Product | Mole Fraction Product | Increase in Chloroform |
|---|---|---|---|---|---|---|---|
| 0.22 | 8.96 | 8.0 | — | — | Methyl chloride | 0.674 | — |
|  |  |  |  |  | Methylene chloride | 0.278 |  |
|  |  |  |  |  | Chloroform | 0.045 |  |
|  |  |  |  |  | Carbon tetrachloride | 0.003 |  |
| 0.28 | 4.70 | 8.8 | 0.244 | 0.45 | Methyl chloride | 0.543 | 100% |
|  |  |  |  |  | Methylene chloride | 0.360 |  |
|  |  |  |  |  | Chloroform | 0.090 |  |
|  |  |  |  |  | Carbon tetrachloride | 0.008 |  |
| 0.30 | 5.04 | 9.2 | 0.238 | 0.59 | Methyl chloride | 0.531 | 113% |
|  |  |  |  |  | Methylene chloride | 0.364 |  |
|  |  |  |  |  | Chloroform | 0.096 |  |

TABLE III-continued

| Mole Fraction Cl₂ | M1/M2 Ratio[1] | Residence Time (Second) | Mole Fraction M2 in Liquid | $n_1/n_0$[2] | Product | Mole Fraction Product | Increase in Chloroform |
|---|---|---|---|---|---|---|---|
| | | | | | Carbon tetrachloride | 0.009 | |

[1] Mole ratio of methyl chloride to methylene chloride.
[2] Liquid mole fraction in total organic feed.

The data in Table 111 above demonstrates that the process of this invention is effective under different process conditions.

What is claimed is:

1. In an improved process for the thermally initiated adiabatic vapor phase chlorination of methyl chloride, methylene chloride and mixtures thereof wherein the improvement comprises injecting a portion of the methyl chloride, methylene chloride or mixtures thereof into a chlorination reactor in the liquid phase using an injecting means which produces a droplet spray having a Sauter mean diameter in the range of at least about 30 microns and no greater than about 200 microns under reaction conditions such that the temperature at essentially all points throughout the reaction zone is maintained at equal to or less than about 500° C. and greater than about 200° C.

2. The process of claim 1 wherein the droplet spray produced has a Sauter mean diameter of no greater than about 100 microns.

3. The process of claim 1 wherein a portion of the methyl chloride is injected as a liquid.

4. The process of claim 1 wherein a portion of the methylene chloride is injected as a liquid.

5. The process of claim 1 wherein a portion of the mixture of methyl chloride and methylene chloride is injected as a liquid.

6. The process of claim 1 wherein at least about 5 percent and no greater than about 60 percent of the methyl chloride, methylene chloride or mixtures thereof is injected as a liquid.

7. The process of claim 1 wherein the liquid is injected using an atomizing nozzle.

8. The process of claim 6 wherein the liquid is injected at a spray angle of at least about 60 degrees.

9. The process of claim 1 wherein the temperature throughout the reaction zone is maintained at less than about 490° C.

10. A process for the thermally initiated vapor phase adiabatic chlorination of a mixture of methylene chloride and methyl chloride comprising the reaction of a mole fraction of chlorine in the feed ranging from about 0.24 to about 0.28 with an organic feed comprising methyl chloride and methylene chloride in a mole ratio ranging from about 1.5 to about 2.0 wherein from about 0.08 to about 0.16 mole fraction of the total organic feed is injected as a liquid and in the absence of additional cooling under conditions such that the temperature throughout the reaction zone is maintained at less than about 490° C. and greater than about 200° C.

11. A process for the thermally initiated vapor phase adiabatic chlorination of a mixture of methylene chloride and methyl chloride comprising the reaction of a mole fraction of chlorine in the feed ranging from about 0.24 to about 0.30 with an organic feed comprising methyl chloride and methylene chloride in a mole ratio ranging from about 4 to about 5 wherein from about 0.40 to about 0.60 mole fraction of the total organic feed is injected as a liquid and in the absence of additional cooling under conditions such that the temperature throughout the reaction zone is maintained at less than about 490° C. and greater than about 200° C.

12. The process of claim 10 wherein the organic feed injected as a liquid is injected as a droplet spray having a Sauter mean diameter in the range of at least about 30 microns and no greater than about 200 microns.

13. The process of claim 11 wherein the organic feed injected as a liquid is injected as a droplet spray having a Sauter mean diameter in the range of at least about 30 microns and no greater than about 200 microns.

* * * * *

REEXAMINATION CERTIFICATE (4121st)

United States Patent [19]
West et al.

[11] B1 5,023,387
[45] Certificate Issued Jul. 18, 2000

[54] LIQUID FEED INJECTION IN A CHLOROMETHANES PROCESS

[75] Inventors: David H. West; Lawrence A. Hebert, both of Baton Rouge; Roger L. Bowlin, Denham Springs; Michael T. Holbrook, Baton Rouge, all of La.

[73] Assignee: The Dow Chemical Company, Midland, Mich.

Reexamination Request:
No. 90/005,520, Sep. 29, 1999

Reexamination Certificate for:
Patent No.: 5,023,387
Issued: Jun. 11, 1991
Appl. No.: 07/517,000
Filed: Apr. 30, 1990

Related U.S. Application Data

[63] Continuation-in-part of application No. 07/342,252, Apr. 24, 1989, abandoned.

[51] Int. Cl.$^7$ .................................................. C07C 17/10
[52] U.S. Cl. ................................................................ 570/252
[58] Field of Search ...................................... 570/252, 255

[56] References Cited

U.S. PATENT DOCUMENTS

| | | |
|---|---|---|
| 3,126,419 | 3/1964 | Burks, Jr. et al. . |
| 3,968,178 | 7/1976 | Obrecht et al. . |

FOREIGN PATENT DOCUMENTS

| | | |
|---|---|---|
| 1443154 | 9/1961 | Germany . |

*Primary Examiner*—Alan Siegel

[57] ABSTRACT

An adiabatic vapor phase chlorination of methylene chloride, methyl chloride or a mixture thereof is improved by the injection of a portion of the methylene chloride, methyl chloride or mixture thereof into the reactor in the liquid state under conditions such that the temperature throughout the reaction zone is maintained at less than about 500° C.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–13 is confirmed.

* * * * *